United States Patent
Madsen (10) Patent No.: US 12,280,231 B2
(45) Date of Patent: Apr. 22, 2025

(54) REVERSIBLE STERILE CONNECTION SYSTEM

(71) Applicant: Fenwal, Inc., Lake Zurich, IL (US)

(72) Inventor: James Madsen, Chicago, IL (US)

(73) Assignee: Fenwal, Inc., Lake Zurich, IL (US)

(*) Notice: Subject to any disclaimer, the term of this patent is extended or adjusted under 35 U.S.C. 154(b) by 818 days.

(21) Appl. No.: 17/220,566

(22) Filed: Apr. 1, 2021

(65) Prior Publication Data

US 2021/0308443 A1   Oct. 7, 2021

Related U.S. Application Data (60) Provisional application No. 63/004,074, filed on Apr. 2, 2020.

(51) Int. Cl.
*A61M 39/16* (2006.01)
*A61L 2/10* (2006.01)
*A61M 39/04* (2006.01)
*A61M 39/10* (2006.01)

(52) U.S. Cl.
CPC ............... *A61M 39/16* (2013.01); *A61L 2/10* (2013.01); *A61M 39/04* (2013.01); *A61L 2202/24* (2013.01); *A61M 2039/1072* (2013.01)

(58) Field of Classification Search
CPC .................. A61M 39/16; A61M 39/04; A61M 2039/1072; A61M 39/1011; A61M 2205/02; A61M 2207/00; A61M 39/10; A61L 2/10; A61L 2202/24
See application file for complete search history.

(56) References Cited

U.S. PATENT DOCUMENTS

| | | | |
|---|---|---|---|
| 4,154,229 A * | 5/1979 | Nugent | A61B 5/154 600/577 |
| 4,157,723 A | 6/1979 | Granzow et al. | |
| 4,334,551 A * | 6/1982 | Pfister | A61M 39/26 604/905 |
| 4,500,788 A | 2/1985 | Kulin et al. | |
| 4,503,333 A | 3/1985 | Kulin et al. | |
| 4,753,697 A | 6/1988 | Shaposka et al. | |
| 4,882,496 A | 11/1989 | Bellotti et al. | |
| 5,009,446 A | 4/1991 | Davis | |
| 5,492,147 A * | 2/1996 | Challender | F16L 37/28 604/905 |
| 6,096,011 A | 8/2000 | Trombley, III et al. | |
| 10,105,529 B2 | 10/2018 | Ryan | |

(Continued)

FOREIGN PATENT DOCUMENTS

| WO | 8302395 A1 | 7/1983 |
|---|---|---|
| WO | WO-8302395 * | 7/1983 |

(Continued)

OTHER PUBLICATIONS

Extended European Search Report and Written Opinion for European Application No. 21166557.5 dated Aug. 30, 2021.

*Primary Examiner* — Theodore J Stigell (74) *Attorney, Agent, or Firm* — Cook Alex Ltd.

(57) ABSTRACT

Sterile connection systems and methods are disclosed. The systems and methods allow for connection of the facing ends of plastic tubing defining flow paths without welding or tube cutting. The two ends may be disconnected, re-sterilized and subsequently reused to make a new sterile connection.

16 Claims, 9 Drawing Sheets

(56) References Cited

U.S. PATENT DOCUMENTS

| | | | |
|---|---|---|---|
| 10,525,249 B2 | 1/2020 | Wegener et al. | |
| 2003/0060804 A1 | 3/2003 | Vaillancourt | |
| 2007/0176117 A1* | 8/2007 | Redmond | A61M 39/16 |
| | | | 250/455.11 |
| 2014/0077488 A1 | 3/2014 | Wegener et al. | |
| 2015/0059901 A1* | 3/2015 | Jin | F16L 37/32 |
| | | | 137/798 |
| 2019/0192844 A1 | 6/2019 | Wegener et al. | |

FOREIGN PATENT DOCUMENTS

| | | |
|---|---|---|
| WO | 8500979 A1 | 3/1985 |
| WO | 2008070220 A1 | 6/2008 |

* cited by examiner

REVERSIBLE STERILE CONNECTION SYSTEM

CROSS-REFERENCE TO RELATED APPLICATION

This application claims the benefit of and priority to U.S. Provisional Patent Application Ser. No. 63/004,074, filed on Apr. 2, 2020, the disclosure of which is incorporated herein by reference in its entirety.

FIELD OF THE DISCLOSURE

The present disclosure is directed to methods and systems for connecting portions of a fluid circuit or administration set in a sterile manner. More particularly, the present disclosure is directed to methods and systems for connecting portions of a fluid circuit/administration set in a sterile manner, and subsequently disconnecting the portions without the need for cutting or severing of the circuit or set. Even more particularly, the present disclosure is directed to methods and systems where a previously made sterile connection between two tubing ends can be disconnected and each end re-sterilized for subsequent connection to a different portion of the same or different circuit/set.

BACKGROUND

Processing, collection and/or delivery of biological fluid such as blood components, biological fluids, or medical fluids may involve using a disposable fluid circuit(s) or administration set(s) adapted for joinder or connection to a source or other containers to establish flow communication between different portions of the fluid circuit, or administration set. The terms "fluid circuit" and "administration set" are used interchangeably herein and to avoid repetition, one or the other term may be used. Use of one term in favor of the other is not meant to exclude the other.

The systems, devices and methods described herein find application in any setting where two previously sterilized portions of a product are sterility joined at a connection site to establish flow communication between the portions. The fluid circuit may include containers such as plastic containers, vials, and associated tubing that define flow paths through the circuit.

When making a connection between two portions of a fluid circuit, sterility must be maintained. In one example, the sterility of the connection site may be assured by exposing the connection site to a sterilization treatment. One such process is described in U.S. Patent Application Publication No. 2019/0192844, the contents of which is incorporated by reference herein.

Alternatively, one or both ends of the connecting flow paths may be sterilized (manually) by the operator just prior to connection. For example, current practice for making fluid flow connections using needleless connectors involves an aseptic process where the exterior surface of the valve, diaphragm or septum of the female connector is manually swabbed with antiseptic prior to insertion of the male connector (which compresses and opens the valve). An example of such a needleless connector is described in U.S. Pat. No. 10,105,529, the contents of which are incorporated herein by reference. Manual swabbing requires increased care by the healthcare professional making the connection. Incomplete swabbing and failure to follow rigorous procedures can potentially result in microorganisms or other contaminants being inadvertently introduced into the fluid path.

Other ways of connecting medical fluid flow tubing involve the irradiation of connectors with ultraviolet light which provides an antibacterial effect on, or sterilization of, the irradiated connector surfaces. Examples of such systems and devices are presented in to U.S. Pat. No. 4,500,788 to Kulin et al.; U.S. Pat. No. 4,503,333 to Kulin et al. and U.S. Pat. No. 4,882,496 to Bellotti et al. The systems and devices of these references, however, are intended for use in specialized settings with connectors of special design.

Still other connection systems for joining fluid flow tubing are also known. For example, tubing connectors that employ heated wafers or elements are known as the SCD® IIB sterile tubing welder available from Terumo BCT of Lakewood, Colorado, and are described in U.S. Pat. No. 4,753,697. Such connection systems may require cutting and heating of the tubing ends in order to make a connection. Other connection systems are described in U.S. Patent Application Publication No. US 2014/0077488 and U.S. Pat. No. 4,157,723.

While these known systems/methods of making a sterile connection involving products in the medical field have generally been effective, it would be desirable to simplify the methods and systems of establishing a sterile connection between tubing ends such that it does not require operator preparation of the connection site by swabbing and disinfecting. It would also be desirable to eliminate the need for cutting or physical welding of the tubing ends. It would further be desirable to provide a method and system of making a sterile connection between two tubing ends that can be disconnected, and the tubing ends re-sterilized and re-used, as necessary.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations, as set forth in the claims appended hereto.

In one aspect, the present disclosure is directed to a fluid circuit that includes a first portion and a second portion joined to the first portion in a sterile manner. The first portion includes tubing attached to a first connecting member at a distal end of the tubing. The first portion connecting member has a base member, a piercing member mount and a piercing member extending from the mount. The first connecting member further includes a housing wherein the mount outer surface and housing inner surface are configured for mating engagement with each other. The housing includes a pierceable septum at its distal end;

The second portion also may include tubing attached to a second connecting member at its distal end. The second connecting member may also include a pierceable septum at a distal end. The second connecting member end further includes one or more engagement members for engaging the first connecting member.

In another aspect, the present disclosure is directed to a method of making a sterile connection between two portions of a fluid circuit of the type described above. The method includes sterilizing the first connecting member, sterilizing the second connecting member and securing the distal end of the first connecting member to the distal end of the second connecting member. Once secured, the method includes advancing the piercing member through the septa of the first and second connecting members to establish flow communication between the two portions.

In another aspect, the connected portions of the fluid circuit can be disconnected and the connecting members re-sterilized for subsequent sterile connection.

DETAILED DESCRIPTION OF THE EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
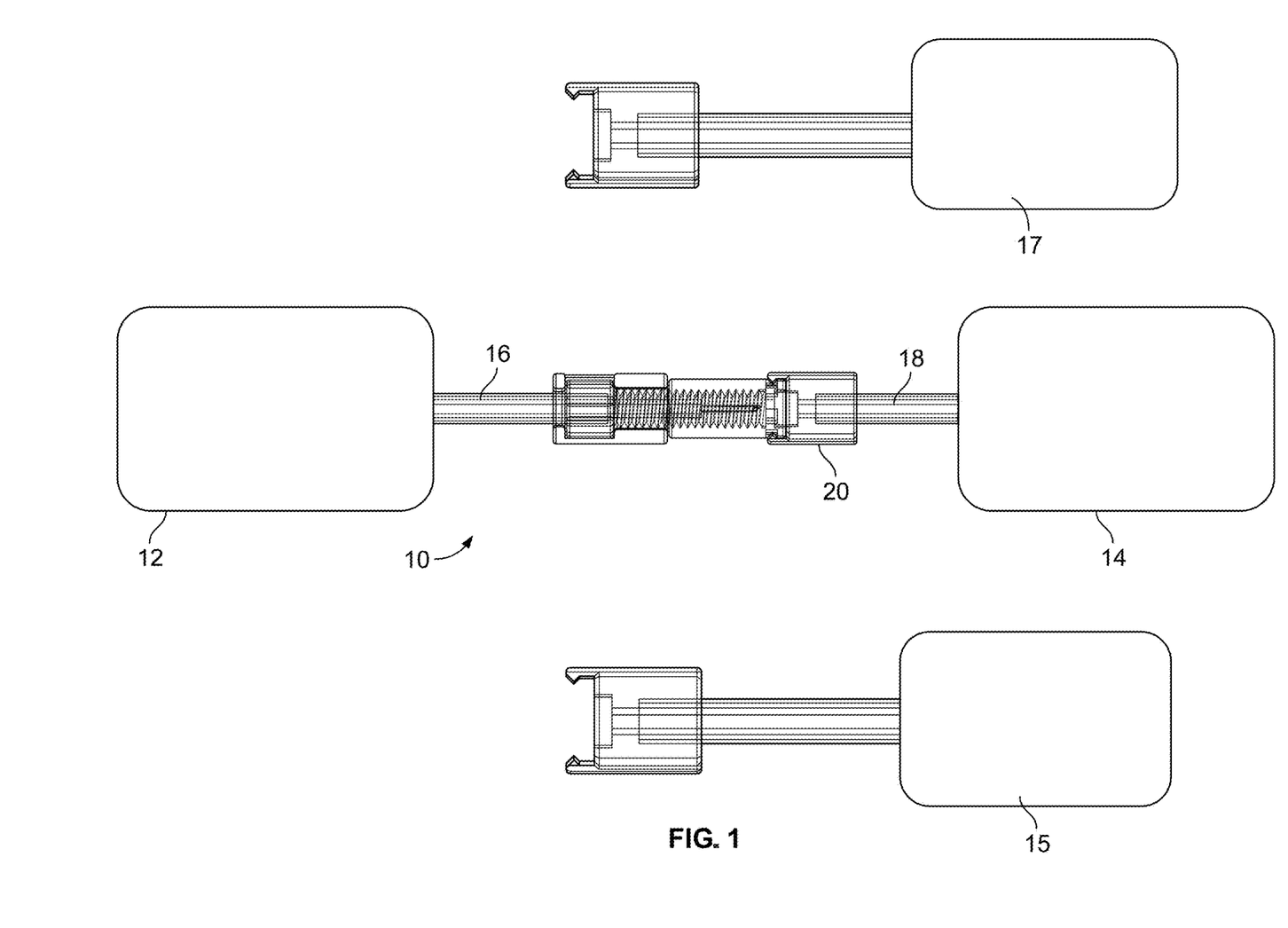
FIG. 1 is a schematic view of multiple portions of a fluid circuit that may be connected in a sterile manner in accordance with the methods and systems described herein.

Turning to the Figures, FIG. 1 shows a fluid circuit 10 in accordance with the present disclosure. Fluid circuit 10 may include a first portion 12 and second portion 14, each portion including any of one or more of containers, tubing defining flow paths, vials, connectors and the like for the processing and/or administration of biological fluid. Ultimately, the two (or more) portions 12, 14 are joined together to form a unitary fluid circuit for carrying out a desired fluid processing or fluid administration procedure. For example, fluid circuit 10 may be used for the administration of a biological fluid to a patient wherein one of the portions includes the biological fluid while the other of the multiple portions includes a fluid delivery device configured to deliver the biological fluid to the subject. The two (or more) portions must be joined together to establish flow communication between the fluid source and the fluid recipient. Other examples where two portions of a fluid circuit are joined together include the collection of a biological fluid from a patient or donor for sampling, treatment or collection. Still other examples of methods and systems of establishing (and reversing) a sterile connection as disclosed herein may be utilized are in distributing a volume of biological fluid from a single container into multiple containers. A reversible sterile connection allows for multiple secondary containers to be connected, filled and disconnected, thereby creating a plurality of smaller fluid volumes from a single, reversible connection point. In any event, the joining of the two portions or containers results in a (sterile) connection site 20 in accordance with the present disclosure.

In the field of cell culturing, the methods and systems of establishing (and reversing) a sterile connection as disclosed herein may be used to add and remove a wash solution from a cell culture device using a single reversible connection site. The reversible seal eliminates the use of traditional and more cumbersome sterile connection steps for each addition or removal of wash media during cell culturing. Similarly, the methods and systems of establishing (and reversing) a sterile connection as disclosed herein may be used in adding/removing cells to a cell culture device to create multiple daughter cell lines in secondary containers from a single mother cell culture.

In one aspect, the connection is reversible in that the two or more portions can be disconnected from one another without the cutting or severing of the tubing(s) 16, 18. In addition, as will be discussed in greater detail below, the connection members associated with each of the portions may be re-usable, allowing for connection to be made with one of the portions 12, 14, disconnection, re-sterilization and connection to a different part of the circuit or to different fluid circuit altogether. For example, as shown in FIG. 1, first portion 12 may be initially connected to second portion 14 to establish fluid communication therebetween. At some point, it may be desired (or required) to establish direct fluid communication between first portion 12 and the second portion 14, but at a different location of the second portion shown, for example, as portion or part 15. Rather than cutting the tubing 16 and/or having to weld or otherwise join tubing to portion or part 15, first and second portion can be disconnected by releasing the mating connecting members (as described in detail below) from each other and establishing a connection between the connecting member of first portion 12 and a corresponding connecting member of portion/part 15. Similarly, if establishing flow communication between fluid circuit 10 and a different kit, component or set is required or desired, first portion 12 may be disconnected, re-sterilized and connected to the separate kit, component or set, shown by reference numeral 17, having a corresponding connecting member.

Figure 2:
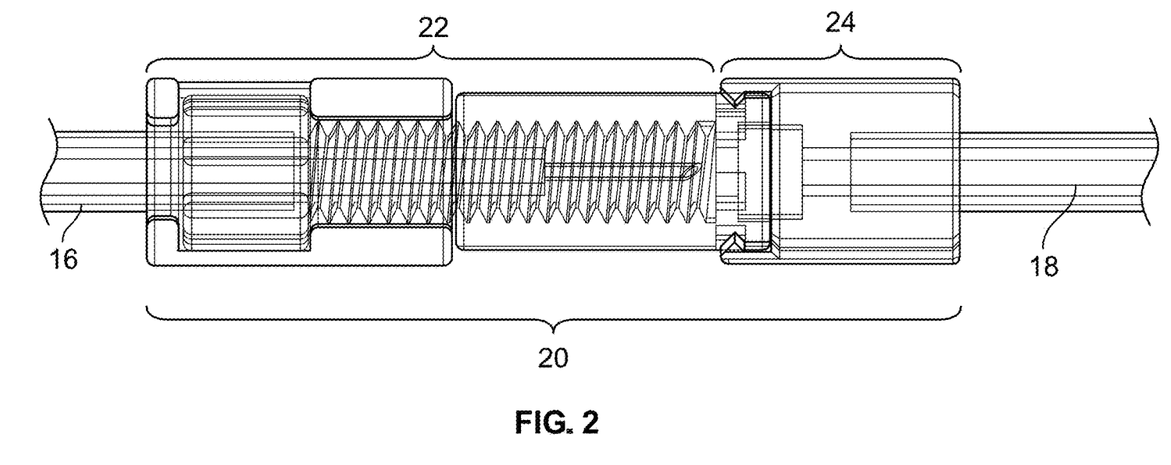
FIG. 2 is an enlarged, longitudinal, side view of the joined connection site in accordance with the present disclosure.

FIG. 2 shows the connection site 20 established in accordance with the present disclosure. Connection site 20 is established by joining (first) connecting member 22 and (second) connecting member 24. Each of connecting members 22 and 24 receives the distal end of tubing(s) 16 and 18, respectively. Distal ends of tubing 16 and 18 may be secured to the respective connecting members by solvent bonding or other means.

Figure 3:
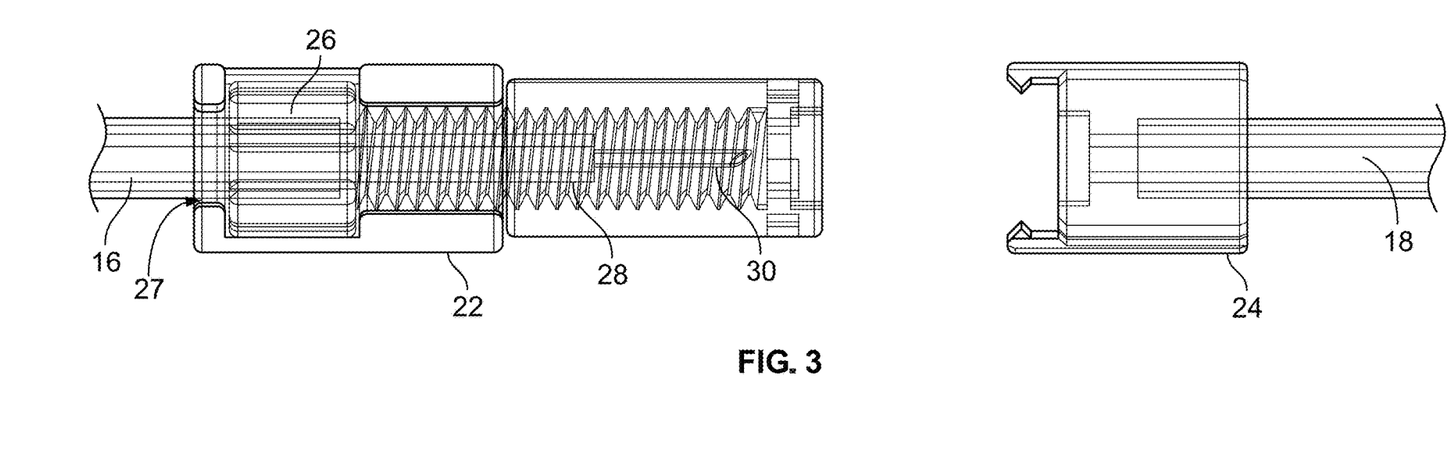
FIG. 3 is a side view of the separated connecting members of first and second portions of a fluid circuit.
Figure 4:
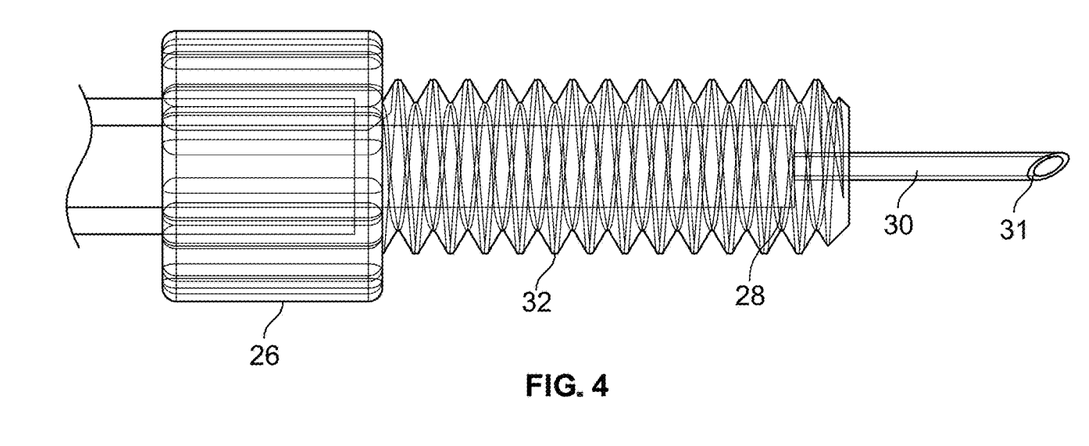
FIG. 4 is a side view of the base member of a first connecting member.
Figure 5:
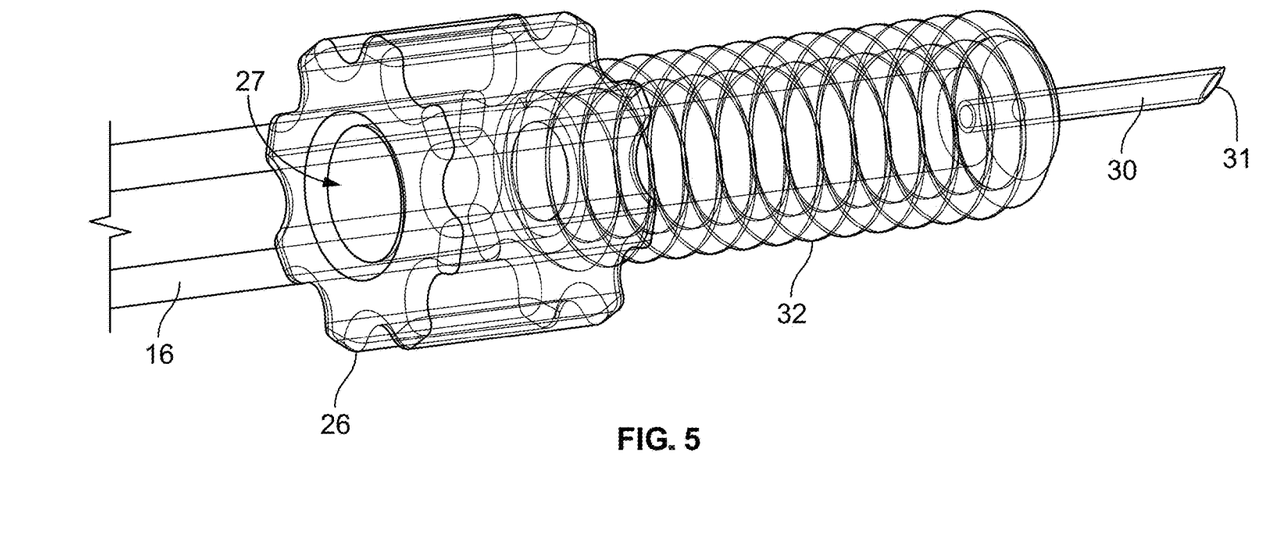
FIG. 5 is a perspective view of the base member of FIG. 4.

FIG. 3 shows connection site 20 in its disconnected state with first connecting member 22 and second connecting member 24. First connecting member 22 includes a central aperture for receiving tubing 16. More particularly, first connecting member 22 includes a rotatable gripping member 26 that defines central aperture 27 that receives distal end of tubing 16 (best seen in FIG. 5). Extending distally from gripping member 26 is a piercing member mount 28 which supports piercing member 30. Mount 28 may be configured for mating engagement with a complimentary member or surface on second connecting member 24 (as will be described below). For example, as best seen in FIG. 4, in one embodiment, needle mount 28 may include an outer surface configured for such mating engagement. In the embodiment of FIG. 4, outer surface 32 may be threaded. Other forms of establishing mating engagement may also be provided such as an annular snap fit arrangement with two mating lip locations, or a cantilever snap fit design with two engagement positions, (for example a piercing member engaged and disengaged), or a ball-and socket snap fit with two similar engagement positions, namely, a piercing member engaged and disengaged. As further seen in FIG. 4, distal tip 31 of piercing member 30 may extend beyond the distal end of needle mount 28.

Piercing member 30 may be a cannula or needle made of a polymeric material or other material. Piercing member 30 terminates in a sharpened distal tip and includes a hollow interior that defines an internal flow path.

As seen in FIGS. 3-4, gripping member 26 may be a generally cylindrical barrel with, preferably, a contoured outer surface that allows for enhanced gripping by the operator during connection. In the embodiment of FIGS. 3-4, the gripping member may be a gear-shaped knob with alternating grooves and ridges.

Figure 6:
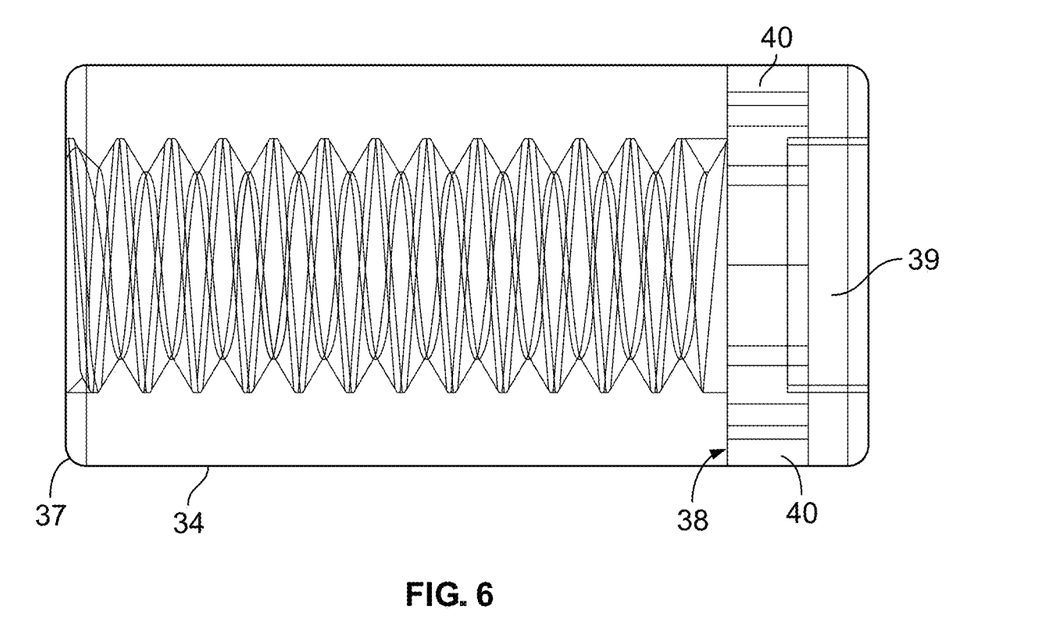
FIG. 6 is a side view of the housing of a first connecting member.
Figure 7:
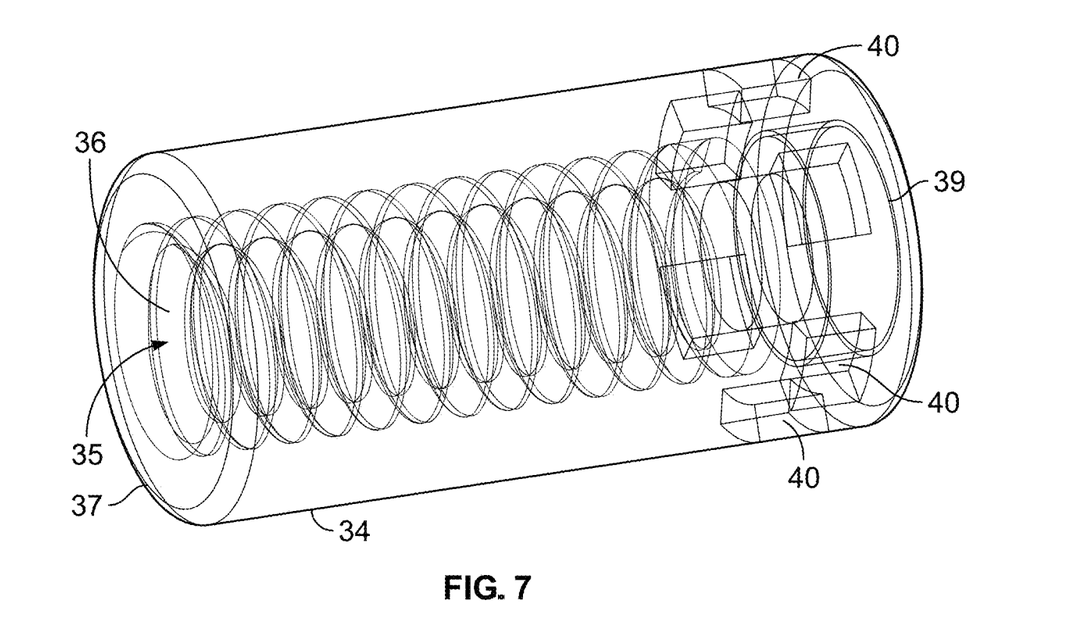
FIG. 7 is a perspective view of the housing of FIG. 6.

First connecting member 22 further includes a housing 34 as seen in FIG. 2 and, in greater detail in FIGS. 6-7. Housing 34 is preferably cylindrical and defines a central bore 35. Inner surface 36 of housing 34 (the surface defining central bore 35) is configured to receive, in mating engagement, the outer surface of mount 28. Thus, for example where needle mount 28 includes a threaded outer surface (as shown in the Figures), inner surface 36 may be correspondingly threaded to receive needle mount 28. The threaded inner surface 36 of housing 34 extends virtually the entire length of the housing, beginning at proximal end 37 and ending at end wall 38 of housing 34, as best seen in FIG. 6.

As further shown in FIGS. 6-7, housing 34 includes a pierceable septum 39 at the distal end of housing 34. Septa of the type used in the device components described herein are well known and are typically made of a resilient, self-sealing elastomer. In addition, end wall 38 includes one or more slots 40 arranged around the circumferential surface of end wall 39. Circumferential slots 40 are configured to receive one or more corresponding engaging member(s) of second connecting member 24, as will be described in greater detail below. Slots 40 may be separated from one another in equidistant intervals. Alternatively, end wall may include a continuous circumferential slot or groove configured to receive one or more engagement members.

Figure 8:
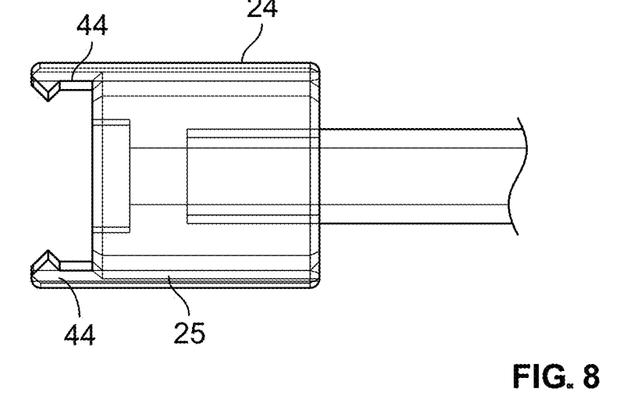
FIG. 8 is side view of a second connecting member.
Figure 9:
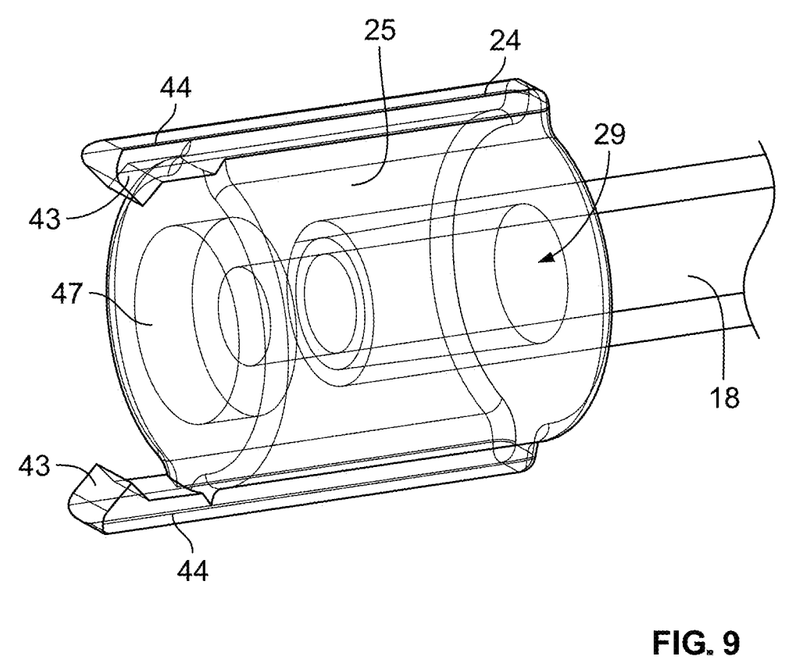
FIG. 9 is a perspective of the second connecting member of FIG. 8.

FIGS. 8-9 show the mating end of second connecting member 24. As with first connecting member 22, second connecting member 24 includes at its proximal end an aperture 29 for receiving tubing 18 of a fluid circuit second portion 14. As described above, distal end of tubing may be solvent bonded to connecting member 24. Second connecting member 24 may define a cylindrical outer wall 25 and a distal end that includes pierceable septum 47. As described above and shown in FIGS. 8-9, second connecting member 24 preferably includes engagement members for engaging corresponding slot(s) 40 or groove located on the outer wall of housing 34. In the embodiment of FIGS. 8-9, engagement members are hooks 43 carried by fingers 44 that extend distally from connecting member 24. Hooks 43 are sized and shaped to enter corresponding slots 40 in a snap fit engagement.

Figure 10:
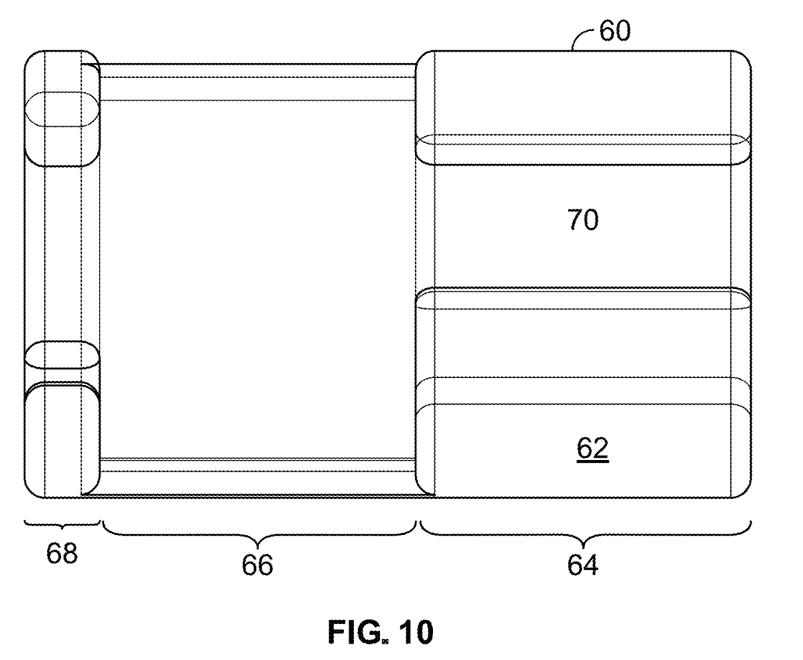
FIG. 10 is a side view of the retaining member.
Figure 11:
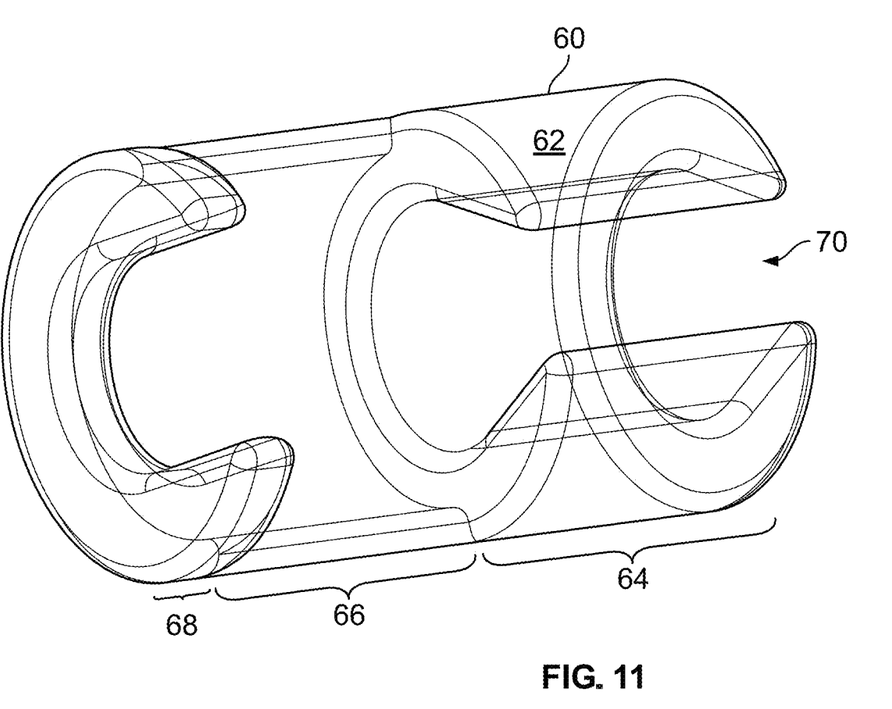
FIG. 11 is a perspective view of the retaining member of FIG. 10.

In accordance with the present disclosure, first connecting member 22 may further include a removable retaining member 60, shown generally in FIG. 3 and in more detail in FIGS. 10-11. Retaining member is configured for placement onto first connecting member 22, in a way that substantially surrounds knob 26 and the distal portion of which abuts housing 34. Retaining member 60 prevents premature advancement of piercing member through housing 34 and into second connecting member 24. In other words, retaining member 60 prevents movement of piercing member in the direction of second connecting member 24 until establishment of fluid flow is desired.

As shown in FIGS. 10-11, retaining member 60 may have a generally cylindrically shaped shape defined by a partial cylindrical wall 62. Wall 62 is deemed partially cylindrical in that the wall 62 does not completely enclose a central aperture of retaining member 60 that receives tubing 16, gripping member 26 and needle mount 28. Wall 62 includes a lead section 64, a central section 66 and end section 68, each section of wall 62 having a gap 70 for receiving the above-identified components of first connecting member 22. For example, gap 70 in lead section 64 should be sufficiently sized to receive needle mount 28 inside the central aperture of retaining member 60. Similarly, gap 70 in end section 68 should be sufficiently sized to comfortably receive tubing 16. In central section 66 of partial wall 62, gap 70 is substantially larger so as to receive and accommodate gripping member 26. When applied in the manner shown in FIG. 3 and as described above, retaining member 60 prevents axial movement of gripping member 26, needle mount 28 and consequently piercing member 30 in the direction of second connecting member 24. Once retaining member 60 is removed, however, rotation of gripping member 26 will advance piercing member 30 and cause further engagement of outer (threaded) surface of needle mount 28 with the corresponding inner (threaded) surface of housing 34. This movement allows piercing member 30 to penetrate the septa and enter second connecting member 24 to establish fluid communication between first and second portions of fluid circuit 10, as described below.

Figure 12:
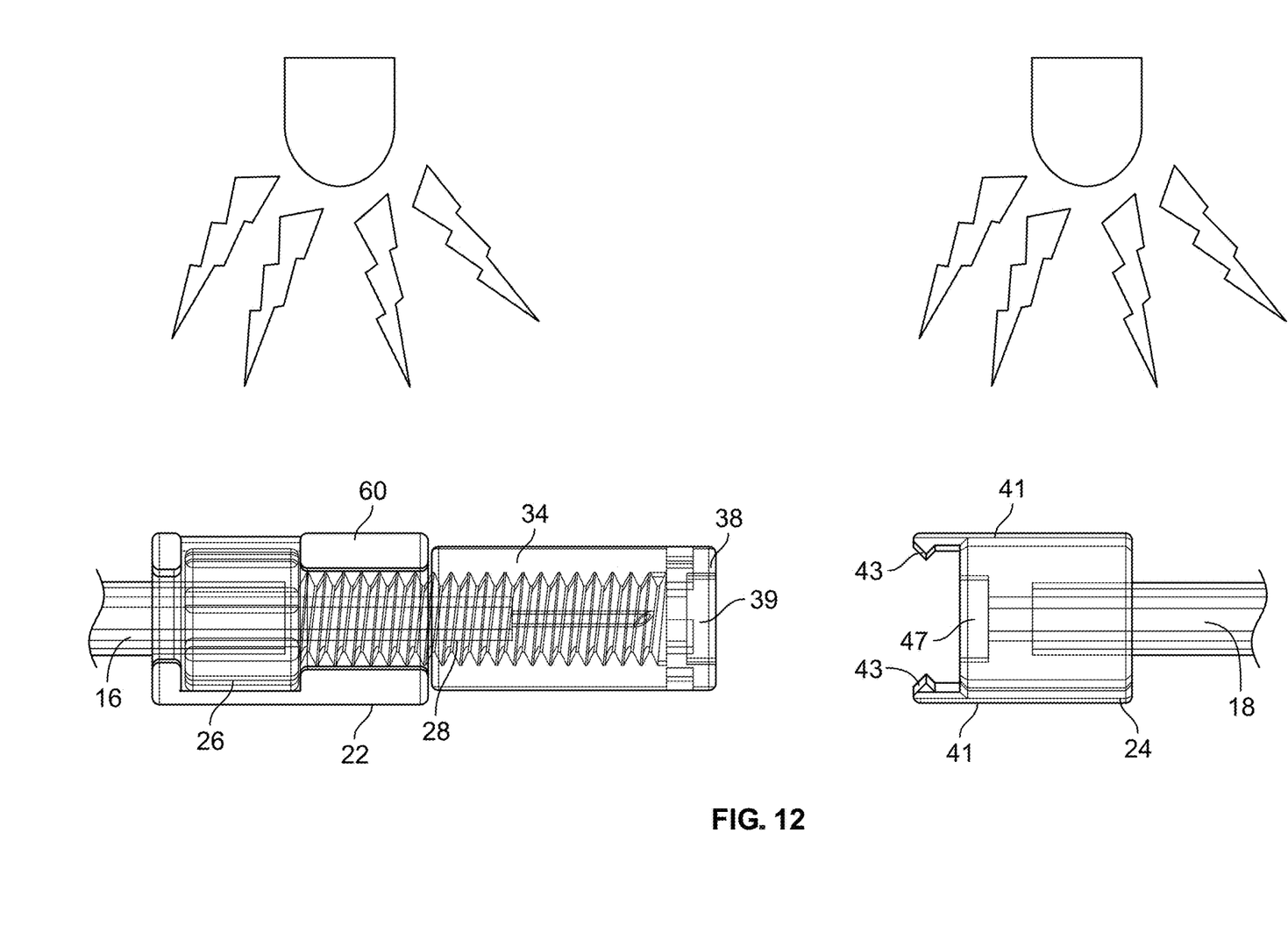
FIG. 12 is a longitudinal, side view of the separated connecting members of first and second portions of a fluid circuit undergoing (radiation) sterilization.
Figure 13:
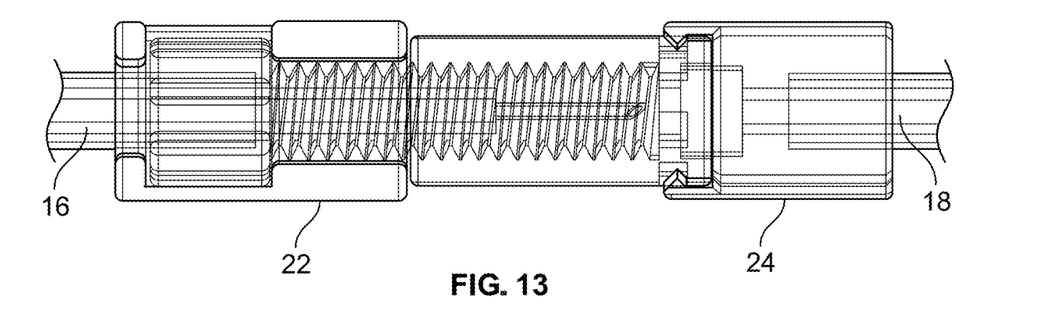
FIG. 13 is a side view of the first and second portion connecting members physically attached to each other prior to establishment of flow communication.

FIGS. 12-18 show the typical steps in the method of making a sterile connection between two initially separate portions of fluid circuit 10. As shown in FIG. 12, the process begins by sterilizing at least the connecting members 22 and 24 of the respective first and second portions 12, 14. The mode of sterilization will depend, in large part, on the material composition of the component parts of connecting members 22 and 24. Where the mode of sterilization includes radiant energy, such as UVC light, the component parts of the first and second connecting members including the gripping member 26 (knob) mount 28, housing 34, retaining clip 60 and second connecting member 24 may be made of a substantially UVC-transparent material such as a cyclic olefinic polymer, poly(methyl methacrylate) Other forms of sterilization may be used such as E-beam, ETO, steam, and the like in the methods and systems for making a reversible sterile connection as described herein, with connecting member materials and geometries adjusted in accordance with such different sterilization techniques, as needed.

First and second connecting members 22 and 24 are separately sterilized by the selected form of sterilization. Sterilization of connecting portions can be carried out simultaneously or sequentially. Devices and methods of sterilization with UVC light are described in U.S. Pat. No. 10,525, 249, the contents of which are incorporated herein by reference. Once sterilized, the facing ends of connecting members 22 and 24 are brought together such that septa 39 and 47 are in contact. As members 22 and 24 are brought into contact, hooks 43 of engagement fingers 44 snap into slots 40 of housing 34 forming connection site 20, shown in FIG. 13. Fingers 44 are sufficiently resilient such that they bend slightly outwardly as they contact end wall 38 of housing 34

Figure 14:
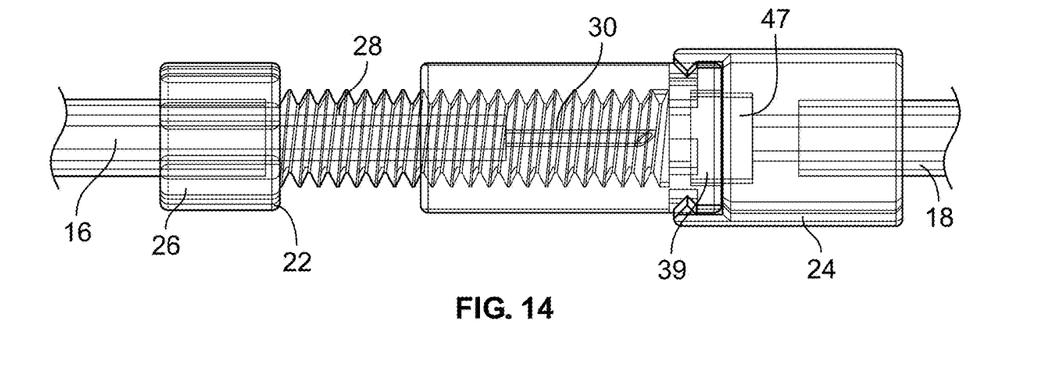
FIG. 14 is the side view of the first and second portion connecting members physical attached to each other with the retaining member removed.
Figure 15:
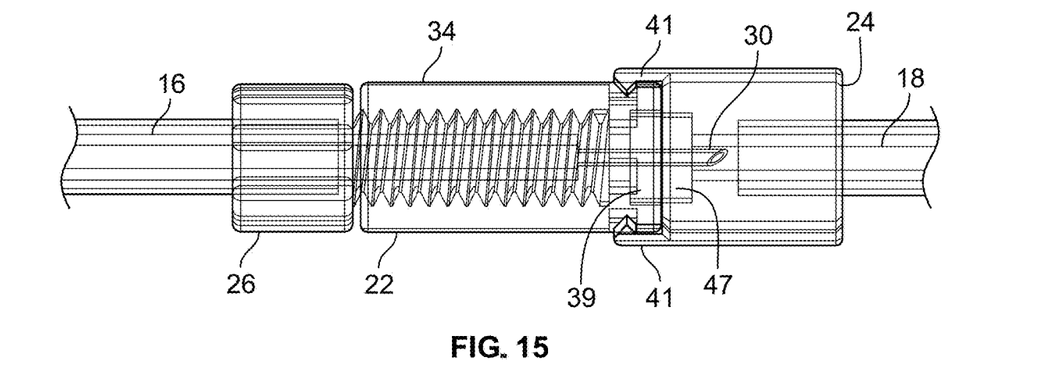
FIG. 15 is a side view of the attached connecting members with the piercing member advanced through the septa of both connecting members.

Once the two connectors 22 and 24 are attached to each other, the steps of establishing fluid communication may commence. To allow for advancement of piercing member 30, retaining member 60 is removed from first connector 22 by simply slipping retaining member off the first connector. The connection site 20 with retaining member 60 removed is thus ready for establishing fluid communication as shown in FIG. 14. By turning gripping member (knob) 26, needle mount 28 with piercing member 30 are advanced further into housing 34. Needle mount 28 with piercing member 30 may be advanced until mount 28 reaches the end of threaded inner surface 36 of housing 34 and piercing member 30 has penetrated septa 39 and 47, as shown in FIG. 15, thus establishing fluid communication between portions 12 and 14.

As indicated above, one of the benefits of the connection system described herein is that connection is reversible. In other words, the two joined portions of the fluid circuit 10 can be disconnected from one another, and the connectors 22 and 24 re-sterilized and re-used to establish a sterile connection with a different part or portion of the circuit or with a portion of a different fluid circuit altogether, as schematically shown in FIG. 1.

Figure 16:
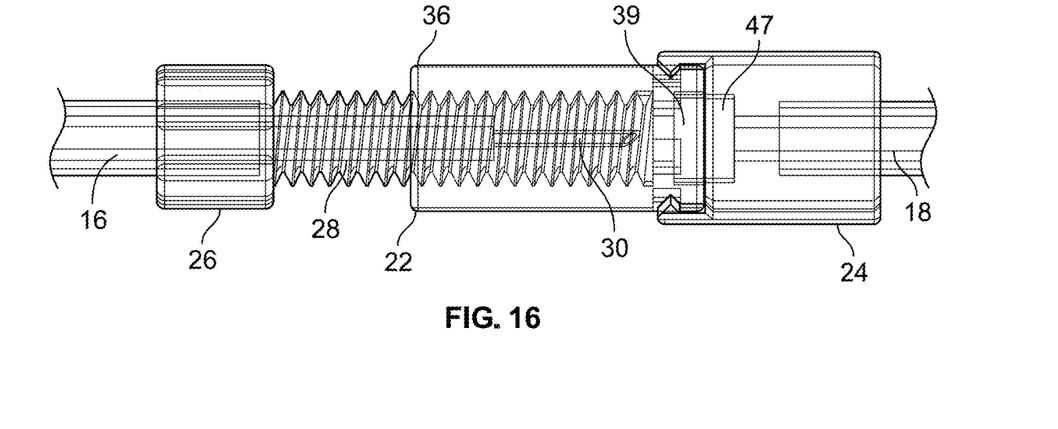
FIG. 16 is a side view of the first and second connecting members physically attached but with the piercing member now removed from the second connecting member and retracted into the housing of the first connecting member.
Figure 17:
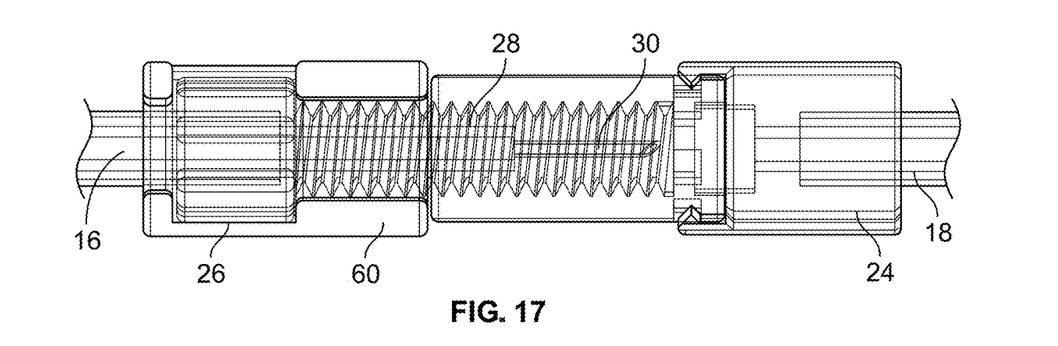
FIG. 17 is a side view of the first and second connecting members physically attached but with the piercing member removed from the second connecting member and retracted within the housing of the first connecting member, with the retaining member replaced on the first connecting member.

As shown in FIG. 16, disconnection begins by rotating gripping member (knob) 26 in a direction opposite to that used to establish fluid communication. Knob 26 is rotated until piercing member is retracted from connector 24, has passed through septa 39 and 47 and resides within housing 34 with the tip of piercing member positioned proximally of end wall 39 such that no part of piercing member 30 extends beyond end wall Once piercing member has been safely retracted into housing 34, retaining member 60 may be placed back onto connector 22 as shown in FIG. 17. This protects against inadvertent movement of base member 26 and piercing member 30 through housing 34. Being able to reinsert retaining member 60 further assures the user that piercing member 30 has been safely retracted and that the piercing member tip is contained within housing 34. Where another form of connection is used, such as the above-described snap fit design (annular, cantilever, ball-and-socket), tactile feedback that the piercing member is retracted may be provided.

Figure 18:
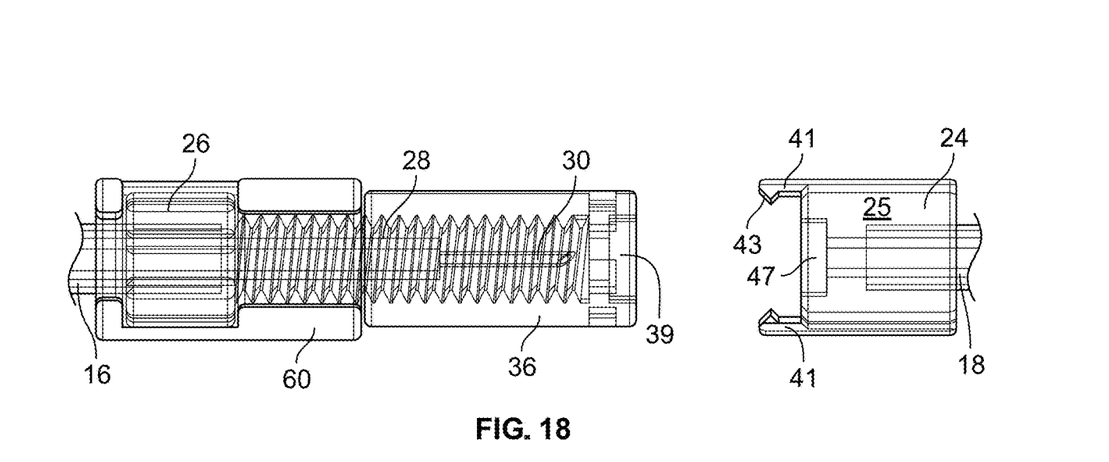
FIG. 18 is a side view of first and second connecting members detached from each other.

Connectors 22 and 24 are then physically disconnected from each other. Outer wall 25 of second connector 24 may be sufficiently compressible such that pressure applied to the wall 25 near the base of fingers 41 causes fingers 41 to bend outwardly and release hooks 43 from slots 42. Connectors 22 and 24 are then pulled apart, as shown in FIG. 18, wherein they can be re-sterilized as shown in FIG. 12.

Other Examples

Aspect 1. A fluid circuit comprising a first portion and a second portion joined to said first portion in a sterile manner wherein: (a) said first portion comprises tubing attached to a first connecting member at a distal end of said tubing, said first portion connecting member comprising a base member, a piercing member mount and a piercing member extending from said mount, said connecting member further comprising a housing, said mount including an outer surface and said housing including an inner surface wherein said mount outer surface and said housing inner surface are configured for mating engagement with each other, said housing having a pierceable septum at its distal end; (b) said second portion comprises a tubing attached to a second portion member at its distal end of said second portion tubing, said second connecting member comprising a pierceable septum at a distal end, said second connecting end further comprising engagement members for engaging said first connecting member.

Aspect 2. The fluid circuit of Aspect 1 further comprising a removable retaining member adapted for placement on said first connecting member between said base and said housing.

Aspect 3. The fluid circuit of any one of Aspects 1 and 2 wherein said mount outer surface comprises an externally threaded surface and said housing inner surface comprises an internally threaded surface.

Aspect 4. The fluid circuit of any one of Aspects 1 through 3 wherein said second connecting member comprises at least one engagement member.

Aspect 5. The fluid circuit of Aspect 4 wherein said first connecting member comprises a receiving member for receiving said engagement member.

Aspect 6. The fluid circuit of any one of Aspects 4 or 5 wherein said at least one engagement member comprises a hook.

Aspect 7. The fluid circuit of Aspect 6 comprising at least one slot for receiving said at least one hook.

Aspect 8. The fluid circuit of any one of Aspects 1 through 7 wherein at least one of said first and second connecting members are made of a material that is sterilizable by radiation sterilization.

Aspect 9. The fluid circuit of Aspect 8 wherein said radiation sterilization comprises UV-C radiation.

Aspect 10. The fluid circuit of any one of Aspects 2 through 9 wherein said retaining member comprises a clip configured for attachment to said first portion.

Aspect 11. The fluid circuit of Aspect 10 wherein said clip comprises a partially cylindrical wall comprising a lead section, a central section and an end section, said lead and end sections defining a central aperture configured to receive said tubing.

Aspect 12. The fluid circuit of Aspect 11 wherein said end section of said partial cylindrical wall includes a gap through which said tubing is press-fit into said aperture.

Aspect 13. The fluid circuit of Aspect 11 wherein said central section of said partially cylindrical wall includes a gap for receiving said base member.

Aspect 14. The fluid circuit of any one of Aspects 1 through 13 wherein said base member comprises a contoured outer surface.

Aspect 15. The fluid circuit of any one of claims 1 through 14 wherein said first and second connecting members comprise a snap fit engagement.

Aspect 16. The fluid circuit of Aspect 15 wherein said snap fit engagement is selected from the group of an annular snap-fit, cantilever snap-fit, and ball-and-socket snap-fit.

Aspect 17. A method of making a sterile connection between two portions of the fluid circuit of any one of Aspects 2 through 16 comprising: sterilizing said first connecting member; sterilizing said second connecting member; securing said distal end of said first connecting member to said distal end of said second connecting member; and advancing said piercing member through said septa of said first and second connecting members.

Aspect 18. The method of Aspect 17 further comprising removing said retaining member prior to advancing said piercing member.

Aspect 19. The method of any one of Aspects 17 and 18 further comprising disconnecting said first and second portions.

Aspect 20. The method of Aspect 19 comprising retracting said piercing member from said second connecting member into said housing of said first connecting member.

Aspect 21. The method of Aspect 20 further comprising attaching said retaining member to said first portion.

Aspect 22. The method of any one of Aspects 17 through 21 comprising repeating steps (a) through (d).

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A fluid circuit comprising a first portion and a second portion joined to said first portion in a sterile and reversible manner wherein:
   a) said first portion comprises tubing attached to a first connecting member at a distal end of said tubing, said first connecting member comprising a base member, a piercing member mount and a piercing member extending from said piercing member mount, said first connecting member further comprising a housing, said piercing member mount including an outer surface and said housing including an inner surface wherein said piercing member mount outer surface and said inner surface of said housing are configured for reversible mating engagement with each other, said housing having a pierceable septum at its distal end, and said first connecting member including a rotatable gripping member comprising a contoured outer surface and coupled to said piercing member mount;
   b) said second portion comprises a second tubing attached to a second connecting member at a distal end of said second connecting member, said second connecting member comprising a pierceable septum at said distal end of the second connecting member, said distal end of said second connecting member further comprising at least one engagement member for engaging said first connecting member.

2. The fluid circuit of claim 1 further comprising a removable retaining member adapted for placement on said first connecting member between said base member and said housing.

3. The fluid circuit of claim 2 wherein said retaining member comprises a clip configured for attachment to said first portion.

4. The fluid circuit of claim 3 wherein said clip comprises a partially cylindrical wall comprising a lead section, a central section and an end section, said lead and end sections defining a central aperture configured to receive said tubing.

5. The fluid circuit of claim 4 wherein said end section of said partially cylindrical wall includes a gap through which said tubing is press-fit into said central aperture.

6. The fluid circuit of claim 4 wherein said central section of said partially cylindrical wall includes a gap sized to accommodate and through which said rotatable gripping member is received.

7. The fluid circuit of claim 6 wherein said rotatable gripping member comprises a cylindrical barrel and a contoured knob.

8. The fluid circuit of claim 1 wherein said piercing member mount outer surface comprises an externally threaded surface and said housing inner surface comprises an internally threaded surface.

9. The fluid circuit of claim 1 wherein said first connecting member comprises a receiving member for receiving said at least one engagement member.

10. The fluid circuit of claim 1 wherein said at least one engagement member comprises a hook.

11. The fluid circuit of claim 10 comprising at least one slot for receiving said hook.

12. The fluid circuit of claim 1 wherein at least one of said first and second connecting members are made of a material that is sterilizable by radiation sterilization.

13. The fluid circuit of claim 12 wherein said radiation sterilization comprises UV-C radiation.

14. The fluid circuit of claim 1 wherein said base member comprises a contoured outer surface.

15. The fluid circuit of claim 1 wherein said first and second connecting members comprise a snap fit engagement.

16. The fluid circuit of claim 15 wherein said snap fit engagement is selected from the group of an annular snap-fit, cantilever snap-fit, and ball-and-socket snap-fit.

* * * * *